(12) United States Patent
Chen et al.

(10) Patent No.: US 6,451,057 B1
(45) Date of Patent: Sep. 17, 2002

(54) SPINAL PLATE ELEMENT ADJUSTING DEVICE HAVING A THREADED ENGAGEMENT

(76) Inventors: Po-Quang Chen, Dept. of Orthopedic Surgery, National Taiwan University Hospital F. Chung-Shan South Road, Taipei (TW); Shing Cheng Wu, 5-1F, No.613, Min Shui Rd., Taipei (TW)

( * ) Notice: Subject to any disclaimer, the term of this patent is extended or adjusted under 35 U.S.C. 154(b) by 0 days.

(21) Appl. No.: 09/984,099

(22) Filed: Oct. 29, 2001

(51) Int. Cl.[7] .................................................. A61F 2/44
(52) U.S. Cl. .................................................. 623/17.15
(58) Field of Search ........................... 623/17.11, 17.15, 623/17.16

(56) References Cited

U.S. PATENT DOCUMENTS 4,863,476 A * 9/1989 Shepperd
5,360,450 A * 11/1994 Giannini
5,390,683 A * 2/1995 Pisharodi ..................... 128/898
5,489,210 A * 2/1996 Hanosh ........................ 433/173
6,129,763 A * 10/2000 Chauvin et al.

* cited by examiner

Primary Examiner—Jeffrey A. Smith

(57) ABSTRACT

A spinal plate element adjusting device having a threaded engagement is provided that includes a cylindrical hollow body and a pushing member having the shape of a frustum of a cone. The outer wall of the body is formed with a threaded portion of predetermined length. The threaded portion is divided into several portions by slits. An outer wall of the pushing member is formed with an external thread for threaded engagement with the internal thread of the body. When the spinal plate element adjusting device is to be implanted between two of the patient's vertebrae, the body is screwed into the area between two vertebrae by the externally threaded portion. By virtue of the taper of the pushing member, the threaded portion of the body is expanded to have a predetermined slope for supporting and buffering the vertebrae of the patient.

5 Claims, 8 Drawing Sheets

US 6,451,057 B1

SPINAL PLATE ELEMENT ADJUSTING DEVICE HAVING A THREADED ENGAGEMENT

FIELD OF THE INVENTION

The present invention relates to a spinal plate element adjusting device having a threaded engagement, wherein the spinal plate element is to be implanted between two of a patient's vertebrae by threaded engagement. By the taper of a pushing member, the threaded portion of the body has a predetermined slope for supporting and buffering the vertebrae of a patient.

BACKGROUND OF THE INVENTION

The vertebrae form a main structure for supporting the human body, especially, it has the function of supporting the body in an upright position and protecting the spinal cord. Each vertebra is supported and buffered by a spinal plate element for providing a shock-proof function.

The spinal plate element can be harmed through injury, diseases or degeneration. Thus, it is necessary to transplant other bone to a damaged vertebra. However, even with the improvements in medical technology that have been made, such a transplant is generally difficult. Furthermore, there is the possibility of infection. Therefore, several man-made spinal plate elements have been developed which can be implanted between the vertebrae of the human body for providing a proper support and reducing the pain of the patients.

Although the prior art man-made spinal plate element has the effect of improving the defects in the prior art, a large force is necessary to push the spinal plate element directly between the vertebrae and thus it is inconvenient to use. Moreover, it is possible for the man-made spinal plate element to be released due to the pressure between the vertebrae.

Therefore, there is a demand for a novel man-made device which will improve the defects in the prior art designs.

SUMMARY OF THE INVENTION

Accordingly, the primary object of the present invention is to provide a spinal plate element adjusting device having a threaded engagement. The spinal plate element adjusting device includes a cylindrical hollow body and a frustro-conically shaped push member. The outer wall of the body is formed with a threaded portion of proper length. The threaded portion is divided into several sections by slits. An outer wall of the push member is formed with an outer thread for threadedly engaging the inner thread of the body. When the spinal plate element is to be implanted between two vertebrae in the human body, the body is screwed into an area between the two vertebrae by the threaded portion. By virtue of the taper of the pushing member, the threaded portion of the body has a predetermined slope for supporting and buffering the vertebrae of a patient.

The various objects and advantages of the present invention will be more readily understood from the following detailed description when read in conjunction with the appended drawings.

DETAILED DESCRIPTION OF THE PREFERRED EMBODIMENTS

To understand the present invention by those skilled in the art, the details of the invention will be described in conjunction with the appended drawings. However, the descriptions made herein are used to aid one for fully understanding the present invention, and should not be used to confine the scope of the present invention as defined in the appended claims.

Figure 1:
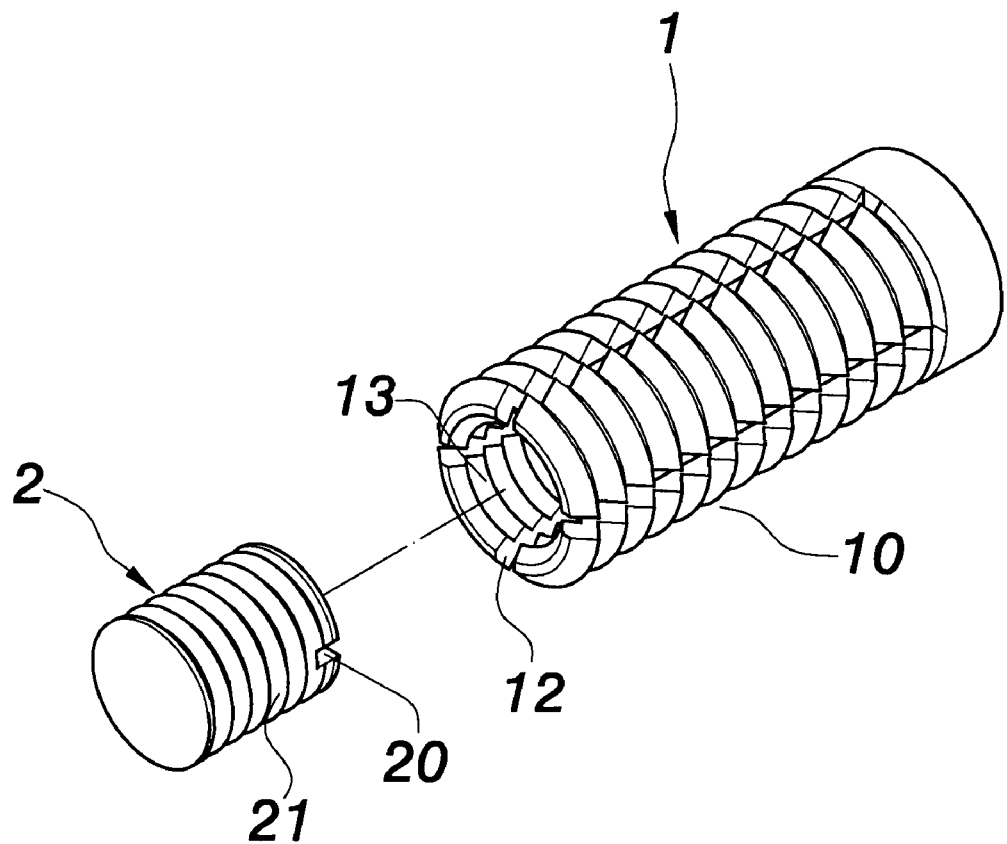
FIG. 1 is an exploded perspective view of the present invention.
Figure 2:
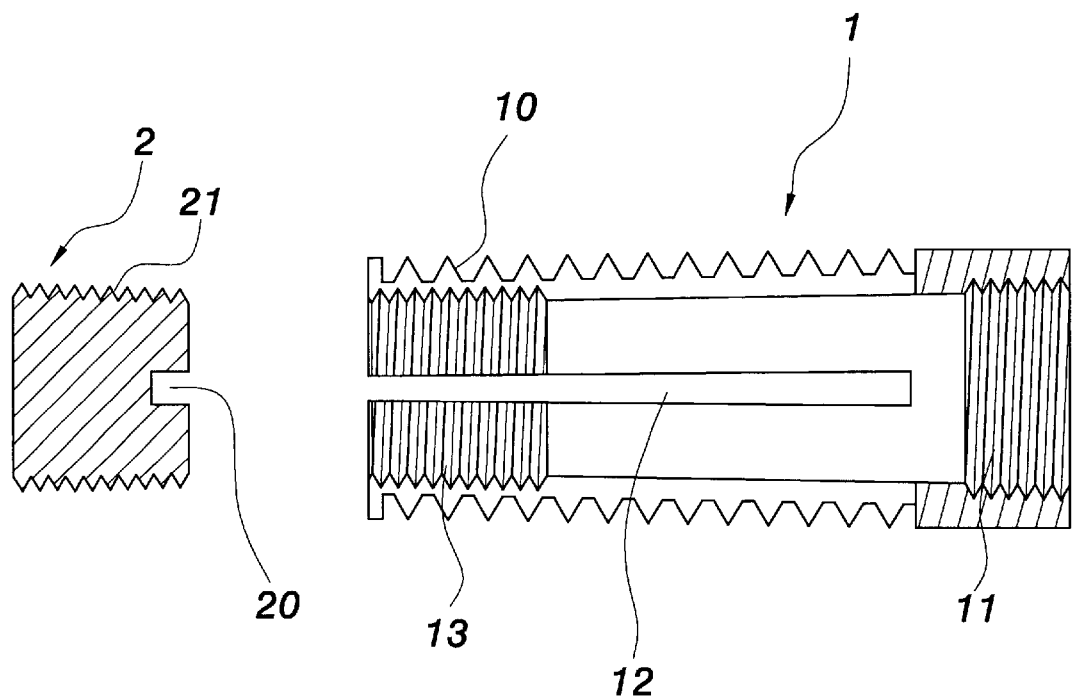
FIG. 2 is a cross-sectional plan view of the present invention.

With reference to FIGS. 1 and 2, the present invention provides a spinal plate element adjusting device having a threaded engagement. The device includes a body 1 and a pushing member 2. The body 1 is a hollow cylinder. A threaded portion 10 is installed at one end of an outer wall thereof. The end surface of the opposing end is installed with a fixing portion 11. The fixing portion 11 has a thread body at a place near the inner wall of the body 1. The threaded portion 10 is divided into four portions by slits 12. The inner wall of the threaded portion 10 is formed with an internal thread 13.

The pushing member 2 is in the shape of a frustum of a cone. The taper is reduced from the front end surface of the pushing member 2 toward the rear portion thereof, along an axial direction. The taper is selectable by a doctor according to the condition of the patient. The rear end surface of the pushing member 2 is installed with a non-round groove 20, which may be in the shape of a straight slot shape, have a cruciform shape, have a rectangular shape, or have a hexagonal shape, etc. A thread 21 is formed in the outer wall. The external thread 21 of the pushing member 2 is threadedly engaged with the internal thread 13 of the body 1. The length of the thread of the internal thread 13 is identical to that of the outer thread 21 so that after being threadedly combined, the front end surface of the pushing member 2 is matched to the front end surface of the body 1. Thereby, a spinal plate element is formed.

Figure 3:
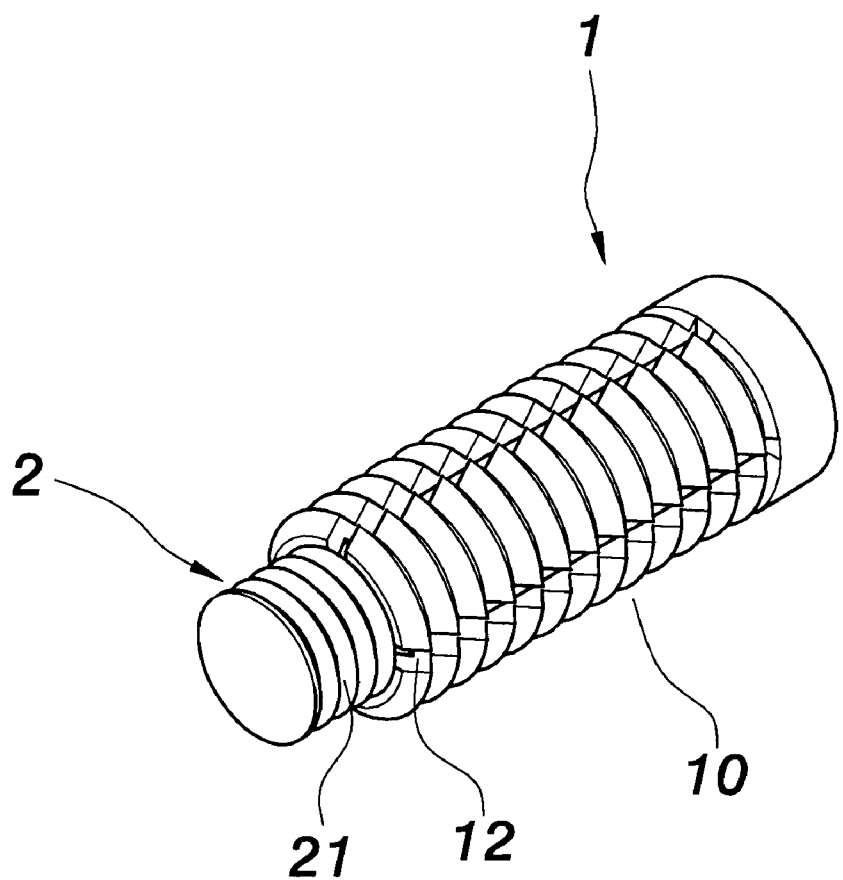
FIG. 3 is an assembled perspective view of the present invention.
Figure 4:
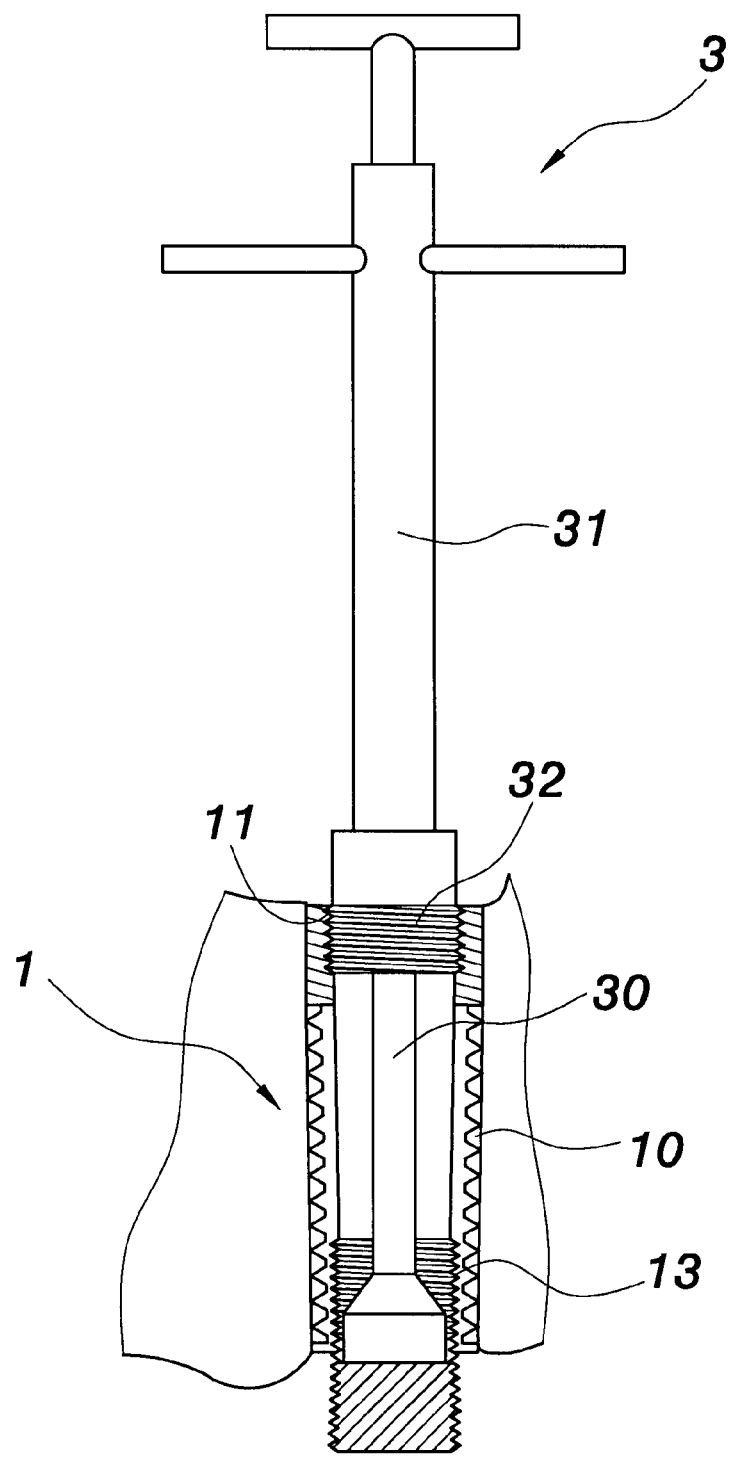
FIG. 4 is a cross-sectional schematic view showing a first step in the use of the present invention.

With reference to FIGS. 3 and 4, when a doctor desires to implant a spinal plate element adjusting device between two vertebrae, an operation rod 3 is used to screw the pushing member 2 into the internal thread 13 of the body 1. The operation rod 3 is formed by a central rod 30 and an outer rod 31. The distal end of the outer rod 31 is installed with a fixing thread 32 for being threadedly engaged with the fixing portion 11 of the body. The outer rod 31 will drive the spinal plate element adjusting device to be threadedly implanted between two vertebrae, and then by engagement of the central rod 30 with the groove 20 of the pushing member 2, the pushing member 2 is rotated to be threadedly advanced along the inner thread 13 of the body 1.

Figure 5:
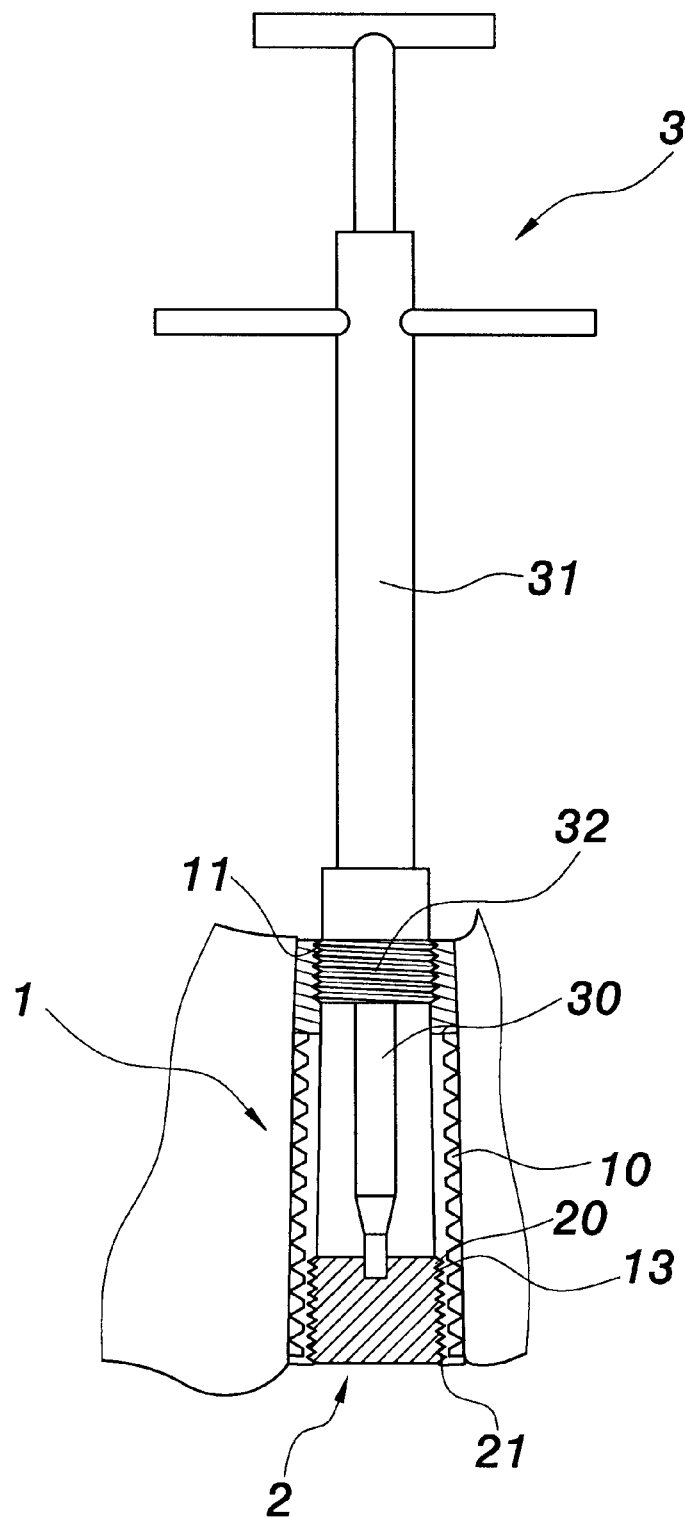
FIG. 5 is a cross-sectional schematic view showing a second step in the use of the present invention.
Figure 6:
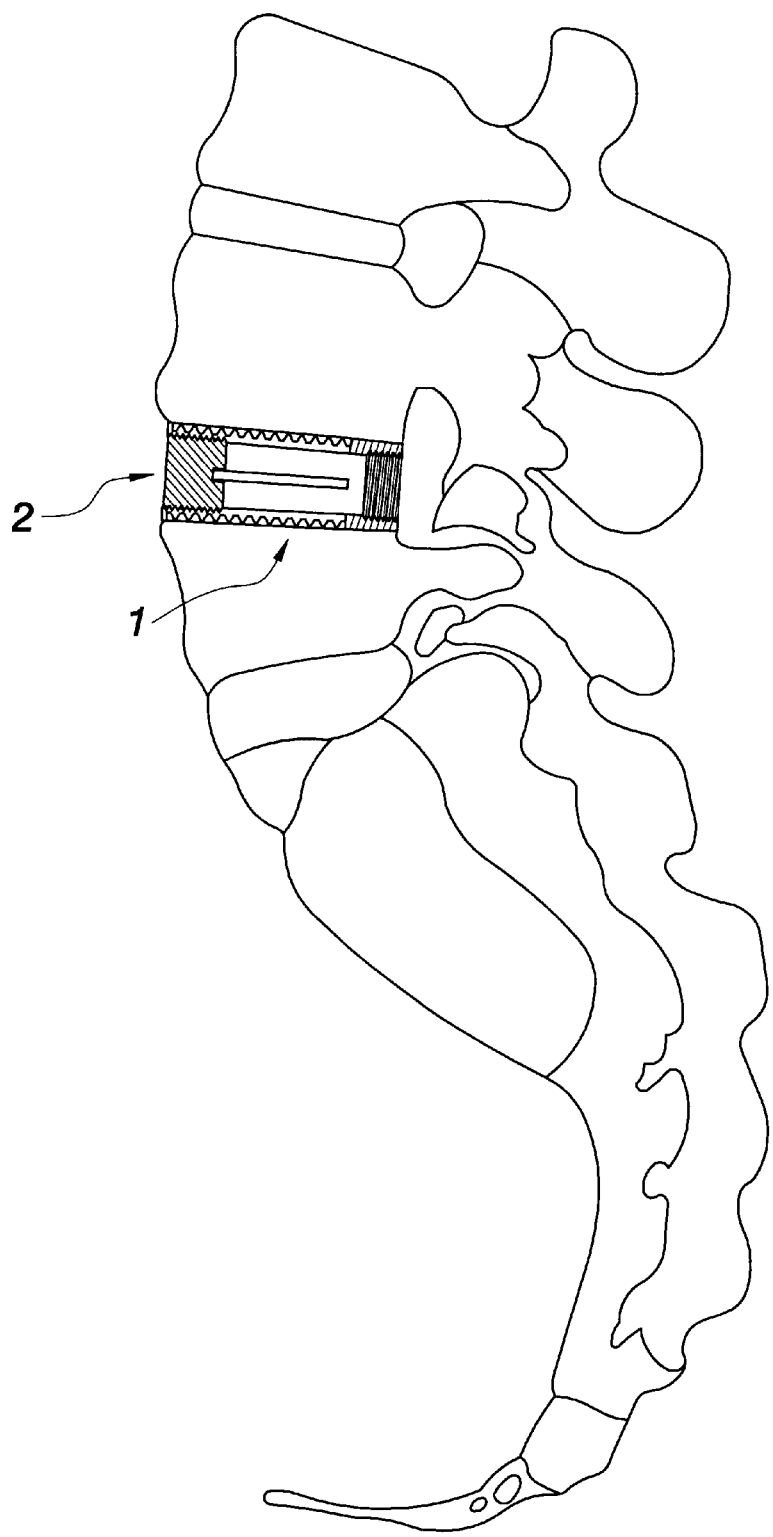
FIG. 6 is a cross-sectional schematic view showing the present invention implanted between two of the vertebrae.

Referring to FIGS. 5 and 6, when the spinal plate element adjusting device is threadedly implanted between two vertebrae, the pushing member 2 is not substantially threadedly engaged with the body 1. The outer rod 31 is used to fix the body 1 so that the central rod 30 serves to screw the pushing member 2 into the body 1 by the helical threads 21 engaged with the threads 13. The threaded portion 10 of the body 1 is divided into four parts by slots 12. The pushing member 2 has a predetermined taper, so that as the pushing member 2 is screwed from the distal end, inwardly, it causes the threaded portion 10 of the body 1 to expand outwards, due to the effect of the taper. The threaded portion 10 will thus be expanded so that the four parts are at an inclined angle. After the pushing member 2 is completely threadedly connected with the body 1, the expansion angle of the body 1 matches that of the taper of the pushing member 2. The front end surface of the body is flush with the front end of the pushing member 2. Therefore, the fixing thread 32 of the outer rod 31 can be unscrewed from the fixing portion 11 of the body 1 so that the spinal plate element adjusting device can be conveniently installed at the preselected position for replacing the original spinal plate of the human body, so as to provide a supporting and buffering function.

Figure 7:
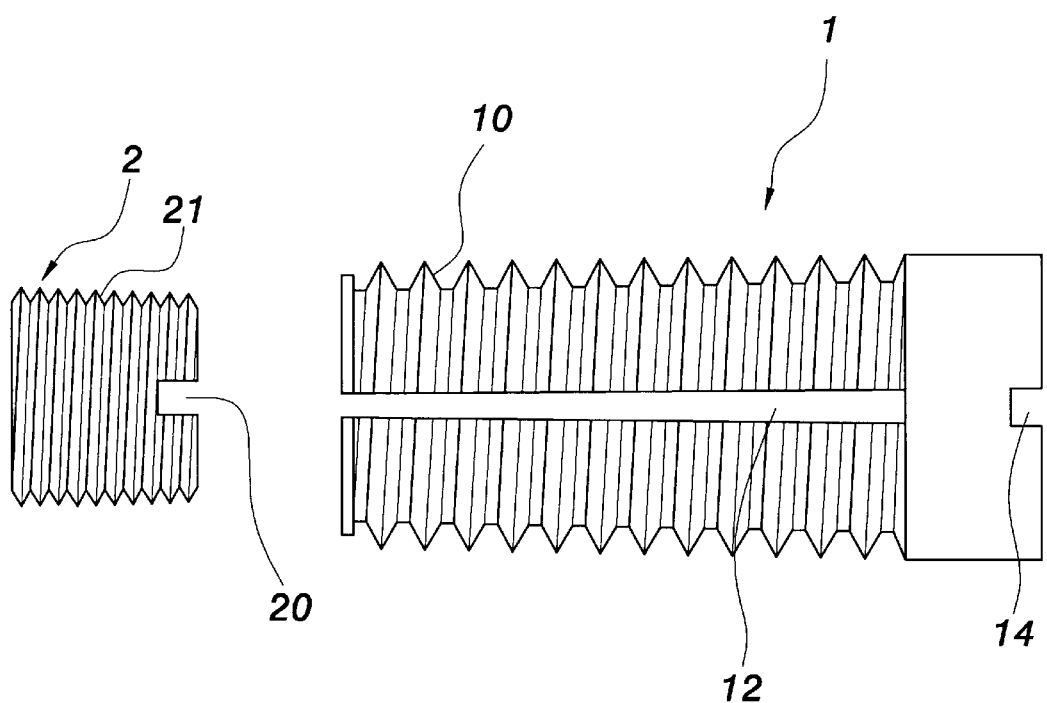
FIG. 7 is an exploded plan view of another embodiment of the present invention.
Figure 8:
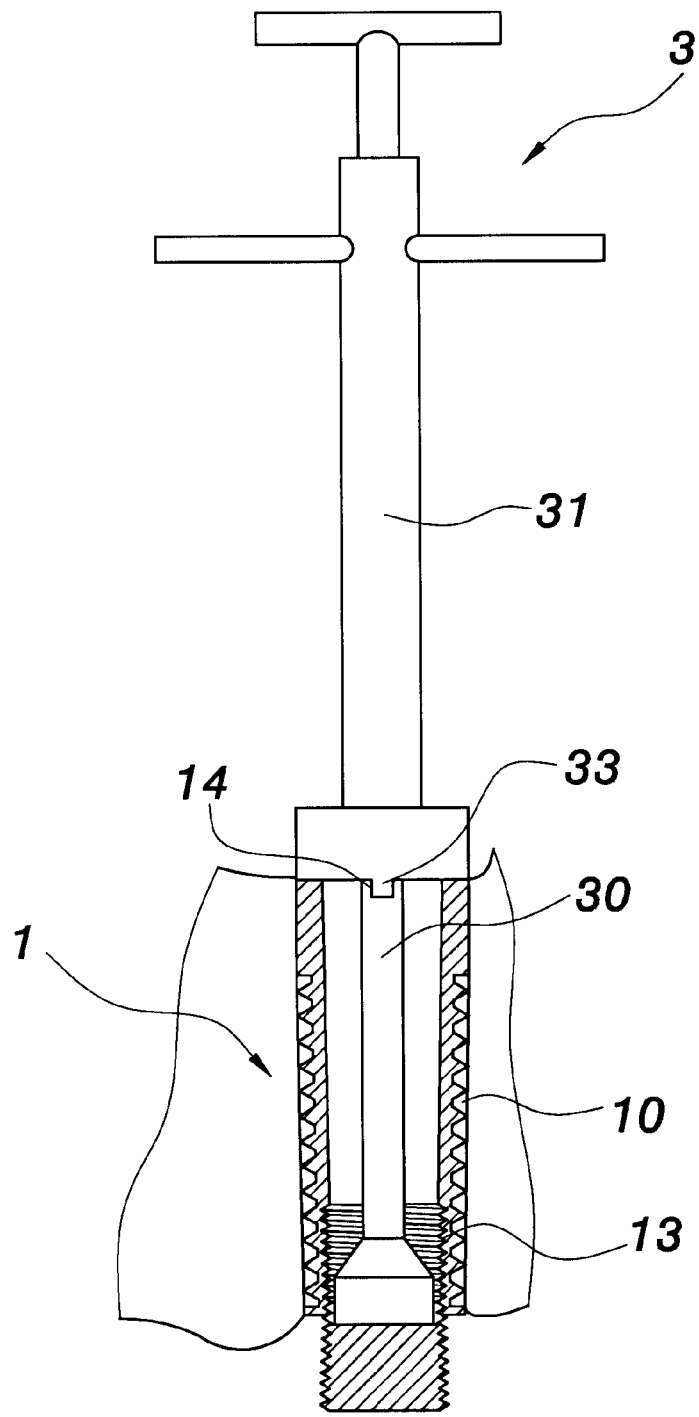
FIG. 8 shows use of the embodiment of FIG. 7.

Additionally, referring to FIGS. 7 and 8, in the present invention, the fixing portion 11 of the body 1 is formed as a non-round concave hole 14, for example, such may be in the form of a straight slot shape, a cruciform shape, a rectangular shape, or a hexagonal shape, etc. The concave hole 14 is formed in the proximal end surface of the body 1. When a doctor desires to implant a spinal plate adjusting device between two of the vertebrae, the distal end of the outer rod 31 of operation rod 3 has a block 33 that corresponds to the concave hole 14 and is engaged therewith. By the engagement of block 33 to fix the body 1, the installation of the spinal plate adjustment device can be accomplished by the aforesaid steps.

In the spinal plate element adjusting device having a threaded engagement of the present invention, the outer wall of the body 1 is formed with a threaded portion 10. Thus, a helical connection method is used to implant the spinal plate element adjusting device between two vertebrae in the human body. Therefore, a convenient implantation method having a high efficiency is provided. Furthermore, by arranging the helical structure of the internal threads of the body in a reverse direction from the external threads of the body, the spinal plate element adjusting device will not be pushed out from between two vertebrae due to a pressure. The pushing member 2 is threadedly connected, so that the body 1 has inclined walls, to provide a preferred support and buffering effect to the patient.

In summary, the present invention is an improvement over the prior art, where the spinal plate element must be implanted with a large force, the operation is inconvenient and it is possible that the spinal plate element will be released from between two of the vertebrae.

Although the present invention has been described with reference to the preferred embodiments, it will be understood that the invention is not limited to the details described herein. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A spinal plate element adjusting device having a threaded engagement for implantation between a pair of vertebrae, comprising:

a longitudinally extended body formed by a hollow cylindrical body, said body having an outer wall surface formed with a threaded portion of predetermined length at a distal end thereof, said body having a fixing portion formed in a proximal end thereof, said threaded portion being divided into a plurality of sections by a plurality of longitudinally directed slits, said distal end having an internal thread formed therein; and a pushing member coupled to said distal end of said body and having a frustro-conical contour to define a predetermined taper of an outer wall surface thereof, said pushing member having a groove formed in a proximal end thereof for receiving an end of a tool therein, said pushing member having an external thread formed in said outer wall surface thereof, said external thread of said pushing member being threadedly engaged with said internal thread of said distal end of said body, wherein the tool releasably engages said fixing portion for rotating said body to threadedly engage said body between a pair of vertebrae, the tool rotating said pushing member relative to said body to longitudinally displace said pushing member toward said proximal end of said body and thereby outwardly expand said plurality of sections of said body.

2. The spinal plate element adjusting device having a threaded engagement as claimed in claim 1, wherein said fixing portion is formed by an internal thread in an inner wall of said proximal end of said body.

3. The spinal plate element adjusting device having a threaded engagement as claimed in claim 1, wherein said fixing portion is formed by a concave hole having a shape selected from a group consisting of a straight slot shape, a cruciform shape, a rectangular shape and a hexagonal shape.

4. The spinal plate element adjusting device having a threaded engagement as claimed in claim 1, wherein said groove of said pushing member having a shape selected from a group consisting of a straight slot shape, a cruciform shape, a rectangular shape and a hexagonal shape.

5. The spinal plate element adjusting device having a threaded engagement as claimed in claim 1, wherein said internal thread of said distal end of said body having a length substantially equal to a length of said external thread of said pushing member, whereby a distal end of said pushing member will be aligned with said distal end of said body when said pushing member is fully engaged with said body.

* * * * *